(12) United States Patent
Quick et al.

(10) Patent No.: US 6,638,884 B2
(45) Date of Patent: *Oct. 28, 2003

(54) COMPRESSIBLE WOOD PULP PRODUCT

(75) Inventors: Robert H. Quick, Sumner, WA (US); Daniel M. Shellhammer, Auburn, WA (US); Michael R. Hansen, Seattle, WA (US); Richard H. Young, Sr., Maple Valley, WA (US)

(73) Assignee: Weyerhaeuser Company, Federal Way, WA (US)

( * ) Notice: Subject to any disclaimer, the term of this patent is extended or adjusted under 35 U.S.C. 154(b) by 172 days.

This patent is subject to a terminal disclaimer.

(21) Appl. No.: 09/836,938

(22) Filed: Apr. 17, 2001

(65) Prior Publication Data

US 2001/0018308 A1 Aug. 30, 2001

Related U.S. Application Data

(63) Continuation of application No. 09/169,705, filed on Oct. 9, 1998, now Pat. No. 6,231,721.

(51) Int. Cl.[7] .................................................. D21H 11/00
(52) U.S. Cl. ........................ 442/417; 442/59; 442/414; 442/394; 162/164.1; 162/174; 162/175; 162/179; 162/181.1; 162/183; 162/184; 162/185
(58) Field of Search ................ 442/414, 417, 442/394, 59; 162/164.1, 174, 175, 179, 181.1, 181.2, 183, 184, 185

(56) References Cited

U.S. PATENT DOCUMENTS

| | | |
|---|---|---|
| 5,147,505 A | 9/1992 | Altman |
| 5,547,541 A | 8/1996 | Hansen et al. |
| 5,582,685 A | 12/1996 | Vinson |
| 5,679,218 A | 10/1997 | Vinson et al. |
| 6,231,721 B1 * | 5/2001 | Quick et al. ............. 162/164.1 |

OTHER PUBLICATIONS

Zobel, Bruce, et al., "Wood and Pulp Properties of Juvenile Wood and Topwood of the Southern Pines," *Applied Polymer Symposium*, No. 28, 1976, pp. 421–433.

* cited by examiner

Primary Examiner—Elizabeth M. Cole
Assistant Examiner—Norca L. Torres
(74) Attorney, Agent, or Firm—Christensen O'Connor Johnson Kindness PLLC

(57) ABSTRACT

A highly densifiable wood pulp product is disclosed. In one embodiment, the densifiable product includes fibers having low coarseness, preferably having a fiber coarseness less than about 22 mg/100 m, and a densifying agent. In another embodiment, the densifiable product further includes fibers having coarseness greater than about 22 mg/100 m. Juvenile wood fibers are the preferred source of fibers having low coarseness. A densified pulp product formed by compacting a fibrous composite that includes fibers having a fiber coarseness less than about 22 mg/100 m, a densifying agent, and optionally, fibers having coarseness greater than about 22 mg/100 m is also disclosed. The pulp products can be advantageously incorporated into absorbent articles and can optionally further include superabsorbent material. Methods for forming the densifiable and densified fibrous products are also disclosed.

70 Claims, 5 Drawing Sheets

COMPRESSIBLE WOOD PULP PRODUCT

CROSS-REFERENCE TO RELATED APPLICATION

This application is a continuation of U.S. patent application Ser. No. 09/169,705, filed Oct. 9, 1998, now U.S. Pat. No. 6,231,721, the benefit of the priority of filing date of which is hereby claimed under 35 U.S.C. §120.

FIELD OF THE INVENTION

The present invention relates to a highly densifiable wood pulp product and methods for its formation and use and, more particularly, to a pulp product that includes fibers having low coarseness.

BACKGROUND OF THE INVENTION

Wood pulp and paper products are conventionally formed from mature wood fiber obtained from mature tree trunks. Mature wood is characterized as having relatively high specific gravity, long and coarse fibers, high cellulose content, and thick cell walls. Mature wood is obtained from the tree trunk or body exclusive of branches and treetops. While mature trees are predominantly composed of mature wood, mature trees also include juvenile wood. Juvenile wood occurs in a zone near the pith at the heart of the tree, extending to the top of the tree, and is present in the first six to eight annual rings from the pith. Wood near the treetop is predominantly juvenile wood.

Because of its generally undesirable characteristics for some products, including low specific gravity, short fibers, low cellulose content, and thin cell walls, juvenile wood is used primarily in pulp and papermaking processes that benefit from its properties. For example, because of the collapsibility of its fibers and improved bonding properties, juvenile wood is used to make some linerboards. Additionally, some juvenile wood is used to make certain printing papers to impart smoothness to the sheet's surface. However, most juvenile wood in the form of treetops, thinnings, and branches is generally discarded at the site of timber harvest in favor of mature wood.

Certain consumer products that include wood pulp fibers require the pulp fiber to be highly compressible and densified, while at the same time maintaining fiber matrix softness. Frequently, these properties are achieved only by the addition of relatively expensive chemical additives, for example, chemicals that disrupt intrafiber hydrogen bonding to reduce fiber stiffness and chemicals that reduce interfiber bonding to reduce web stiffness. The addition of large quantities of chemicals to wood pulp is economically disadvantageous.

Accordingly, a need exists for wood pulp products that can be highly compressed and densified while maintaining fiber softness with minimal addition of expensive chemicals. A need also exists for optimizing and efficiently utilizing forest resources including previously underutilized forest products. The present invention seeks to fulfill these needs and provides further related advantages.

SUMMARY OF THE INVENTION

In one aspect, the present invention provides a densifiable wood pulp product. In one embodiment, the densifiable product is a compressible fibrous composition that includes fibers having low coarseness, preferably having a fiber coarseness less than about 22 mg/100 m, and a densifying agent. In another embodiment, the densifiable product further includes fibers having coarseness greater than about 22 mg/100 m. Juvenile wood fibers are the preferred source of the fibers having low coarseness.

In another aspect, the invention provides a densified pulp product formed by compacting a fibrous composition that includes fibers having a fiber coarseness less than about 22 mg/100 m, a densifying agent, and optionally, fibers having coarseness greater than about 22 mg/100 m.

The products of the invention can be advantageously incorporated into absorbent articles such as diapers, feminine care products, and adult incontinence products. Thus, in further aspect, the invention provides absorbent articles that incorporate the fibrous products of the invention. In these applications, the products can optionally include absorbent material such as superabsorbent polymeric material.

Methods for forming the densifiable and densified fibrous products of the invention are also provided.

BRIEF DESCRIPTION OF THE DRAWINGS

The foregoing aspects and many of the attendant advantages of this invention will become more readily appreciated by reference to the following detailed description, when taken in conjunction with the accompanying drawings, wherein.

DETAILED DESCRIPTION OF THE PREFERRED EMBODIMENT

Figure 1:
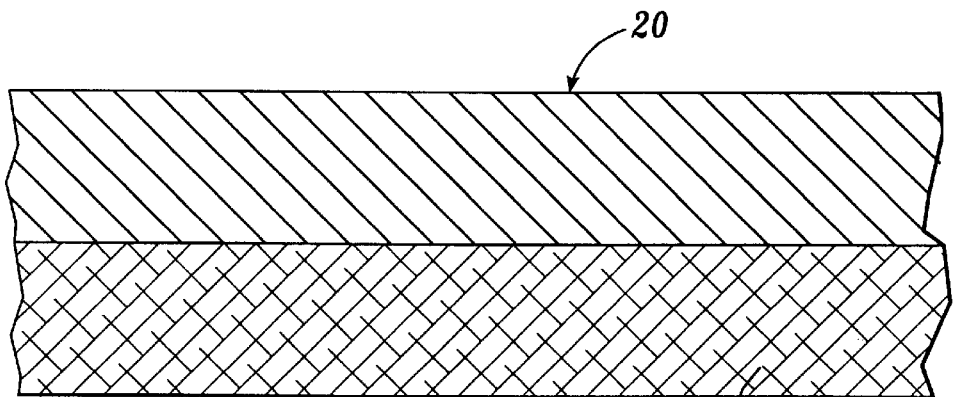
FIG. 1 is a cross-sectional view of a portion of an absorbent construct incorporating a composite formed in accordance with the present invention and an acquisition/distribution layer.

The present invention provides a highly compressible wood pulp product, a densified product formed from the compressible product, and methods for their formation and use. The pulp products include fibers having low coarseness and a densifying agent. Fibers having low coarseness preferably include juvenile wood fibers that can be obtained from select juvenile woods and juvenile wood recovered from thinnings and residual tops of loblolly pine trees. In one embodiment, the wood pulp product of the invention includes a blend of fibers having low coarseness and fibers having high coarseness, preferably a blend of juvenile wood fibers and mature wood fibers, respectively, and a densifying agent. In another embodiment, the invention provides a pulp product that includes fibers having low coarseness and a densifying agent. The inclusion of fibers having low coarseness in these products provides for a reduction in the amount of chemical additives typically necessary to form highly compressible, densified pulp products that maintain fiber softness and that are conventionally used in the production of consumer absorbent articles.

The wood pulp products of the invention include fibers having relatively low coarseness. As used herein, "fiber coarseness" refers to fiber coarseness values that can be measured and determined by a variety of methods and procedures known to those in the art, including the Kaajani and Fiber Quality Analyzer (FQA) methods. Fibers having low coarseness useful in forming the products of the present invention include fibers having a fiber coarseness less than about 22 mg/100 m, preferably from about 6 to about 20 mg/100 m, and more preferably from about 7 to about 18 mg/100 m. The low coarseness fibers suitable for the invention can be obtained from wood sources including juvenile wood, such as juvenile southern pine, and juvenile and mature northern softwood. Juvenile wood is a preferred source of fibers having low coarseness. Generally, most mature wood fibers are fibers having fiber coarseness values greater than about 22 mg/100 m.

Juvenile wood fibers useful in forming the product of the present invention are preferably obtained from southern pine (e.g., loblolly pine). Juvenile wood fibers can be obtained from treetops that are preferably less than about 7.5 years old and tree thinnings preferably less than about 15 years old. Juvenile wood fibers can also be obtained from select juvenile trees.

Juvenile wood fibers have a lower coarseness than mature wood fibers. For example, the coarseness of fibers obtained from 7.5-year-old tops of 30-year-old trees and for 15-year thinnings was determined by the FQA method (using a device manufactured by OpTest Equipment, Hawkesbury, Ontario, Canada) to be about 18 mg/100 m and about 22 mg/100 m, respectively. In contrast, fiber coarseness for fibers from 30-year-old trees (i.e., harvested trees without their tops) was measured and determined to be 24 mg/100 m. In addition to differences in fiber coarseness, juvenile wood fibers are also shorter than mature wood fibers. For example, fiber length measured by the FQA method for 7.5-year-old tops obtained from 30-year-old trees and for 15-year thinnings was found to be about 2.1 mm and about 1.9 mm, respectively. These lengths are significantly less than those of mature wood fibers obtained from 30-year-old trees which were found to have a fiber length of about 2.7 mm.

In one embodiment, the pulp product of the present invention preferably includes a blend of fibers having low coarseness and fibers having high coarseness, preferably a blend of juvenile and mature wood fibers. In this embodiment, fibers having low coarseness (e.g., juvenile wood fibers) are preferably present from about 10 to about 50 percent by weight, and preferably from about 20 to about 40 percent by weight, based on the total weight of fibers. In a more preferred embodiment, fibers having low coarseness are present in about 30 percent by weight of the total weight of fibers. Generally, pulp products that contain less than about 10 percent by weight fibers having low coarseness do not possess the advantageous densification properties discussed below. Manufacturing pulp products that contain greater than about 50 percent by weight fibers having low coarseness for fluff applications leads to other attendant disadvantages such as high fiberization energies, increased chemical requirement, and poor airlaid pad integrity.

The advantageous densification properties observed for the pulp products of the present invention can be attributed to the presence of fibers having low coarseness. The pulp products can be formed by combining fibers having low coarseness (e.g., juvenile wood fibers) and fibers having high coarseness (e.g., mature wood fibers) to provide a fibrous pulp product containing from about 10 to about 50 percent by weight fibers having low coarseness. Alternatively, fibers having low coarseness and fibers having high coarseness can be coprocessed to provide a fibrous product that includes a blend of wood fibers. In such a method, the coprocessing of fibers having low coarseness and fibers having high coarseness does not require the segregation of fibers having low coarseness from fibers having high coarseness. The combined harvest of juvenile and mature woods can be simultaneously processed to provide the fibrous wood product of the present invention.

The fibrous product of the present invention can be formed by conventional pulp sheet and paper manufacturing methods including handsheet and manufacturing line forming methods. Preferably, the fibrous product of the present invention is formed on a wet-laid pulp sheet manufacturing line. Briefly, a pulp sheet manufacturing line includes delivering a pulp slurry from a headbox through a slice and onto a forming wire (i.e., foraminous support). In addition to fibers having low coarseness and fibers having high coarseness, the pulp slurry can include other fibers such as, for example, crosslinked cellulosic fibers, synthetic fibers, or other noncellulosic fibers. Additionally, the pulp slurry can contain other additives such as debonders, surfactants, absorbent material such as superabsorbent particles, and fillers. Water is then drawn from the deposited pulp on the wire by a vacuum system leaving a deposited, partially dewatered pulp sheet that can then be conveyed to a subsequent dewatering station such as, for example, a set of one or more calender rolls, each defining a nip through which the pulp sheet passes. From the dewatering station, the pulp sheet enters a drying station that can include, for example, multiple canister dryers and/or through-air dryers. The dried pulp sheet emerging from the drying section typically has a moisture content of about 10 percent by weight of the fibers, preferably about 6 to about 8 percent by weight moisture. The dried sheet can then typically be treated with any further additives desired to impart a particular range of properties and then taken up on a roll for transportation to a remote location, such as at a user's plant for use in manufacturing products. Alternatively, the dried sheet can be collected in a baling apparatus from which bales of the pulp can be obtained for transport to a remote location.

As noted above, certain absorbent properties of absorbent consumer articles such as infant diapers, adult incontinent products, and feminine care products, derive from the wood pulp fibers contained within the products. Generally, fiber softness is advantageous and desired for user comfort. Ideally, the absorbent product also rapidly acquires and permanently stores liquid exudates. The advantageous absorbent properties of these consumer products arise, at least in part, from the relatively high compressibility and densification of the component wood pulp fibers. However, such high compression and densification result in a decrease in the absorbent articles' softness. Consequently, highly compressed and densified fibers and fibrous composites typically require the addition of relatively expensive chemical additives, or secondary mechanical processing, to maintain fiber softness. The present invention provides for the use of select sources of naturally occurring wood fibers (i.e., fibers having low coarseness such as juvenile wood fibers) to replace and reduce the amount of chemical additives required to provide a soft yet compressed and densified absorbent fibrous product.

The fibrous product of the present invention also includes a densifying agent. Suitable densifying agents include those described in U.S. Pat. No. 5,547,541, issued to Hansen et al., which is expressly incorporated herein by reference. The densifying agent includes a functional group that is capable of forming a hydrogen bond with cellulosic fibers. In a preferred embodiment, the densifying agent further includes a second functional group that is capable of forming a hydrogen bond or a coordinate covalent bond with a particle, (e.g., a superabsorbent polymer) such as those that may be combined with the densifying agent-treated fibers of the present invention to form absorbent articles.

The densifying agent is preferably present in the fibrous product in an amount from about 0.1 to about 15 percent by weight of the fibrous product. More preferably, the densifying agent is present in an amount from about 0.5 to about 10 percent, and most preferably from about 0.7 to about 9 percent by weight of the total product.

Suitable densifying agents include polymeric and non-polymeric densifying agents. Included among the nonpolymeric densifying agents are organic and inorganic densifying agents. Other suitable densifying agents include materials that are hygroscopic in nature.

As noted above, a method for densifying fibers using such densifying agents is described in U.S. Pat. No. 5,547,541. Binding agents for fibers and the use of these agents to bind particles to fibers and to enhance the densification of fibers treated with these agents is described in U.S. patent application Ser. No. 08/416,375, filed Apr. 4, 1995, assigned to Weyerhaeuser Company, and expressly incorporated herein by reference.

Other suitable particle binders and/or densification/softness aids useful as densifying agents and processes for combining them with cellulose fibers are disclosed in the following U.S. patents: (1) U.S. Pat. No. 5,543,215, entitled "Polymeric Binders for Binding Particles to Fibers"; (2) U.S. Pat. No. 5,538,783, entitled "Non-Polymeric Organic Binders for Binding Particles to Fibers"; (3) U.S. Pat. No. 5,300,192, entitled "Wet Laid Fiber Sheet Manufacturing With Reactivatable Binders for Binding Particles to Binders"; (4) U.S. Pat. No. 5,352,480, entitled "Method for Binding Particles to Fibers Using Reactivatable Binders"; (5) U.S. Pat. No. 5,308,896, entitled "Particle Binders for High-Bulk Fibers"; (6) U.S. Pat. No. 5,589,256, entitled "Particle Binders that Enhance Fiber Densification"; (7) U.S. Pat. No. 5,672,418, entitled "Particle Binders"; (8) U.S. Pat. No. 5,607,759, entitled "Particle Binding to Fibers"; (9) U.S. Pat. No. 5,693,411, entitled "Binders for Binding Water Soluble Particles to Fibers"; (10) U.S. Pat. No. 5,547,745, entitled "Particle Binders"; (11) U.S. Pat. No. 5,641,561, entitled "Particle Binding to Fibers"; (12) U.S. Pat. No. 5,308,896, entitled "Particle Binders for High-Bulk Fibers"; (13) U.S. Pat. No. 5,498,478, entitled "Polyethylene Glycol as a Binder Material for Fibers"; (14) U.S. Pat. No. 5,609,727, entitled "Fibrous Product for Binding Particles"; (15) U.S. Pat. No. 5,571,618, entitled "Reactivatable Binders for Binding Particles to Fibers"; (16) U.S. Pat. No. 5,447,977, entitled "Particle Binders for High Bulk Fibers"; (17) U.S. Pat. No. 5,614,570, entitled "Absorbent Articles Containing Binder Carrying High Bulk Fibers; (18) U.S. Pat. No. 5,789,326, entitled "Binder Treated Fibers"; and (19) U.S. Pat. No. 5,611,885, entitled "Particle Binders", all expressly incorporated herein by reference.

Polymeric densifying agents include polymeric compounds having at least one hydrogen bonding functionality. In accordance with the present invention, the polymeric densifying agents can be a polyglycol, a polycarboxylic acid or polycarboxylate, a poly(lactone) polyol, a polyamide, a polyamine, a polysulfonic acid or a polysulfonate, combinations thereof, and copolymers that include nonhydrogen bonding monomer units in the polymeric chain. Specific examples of certain of these densifying agents include: polyglycols such as polypropylene glycol and polyethylene glycol; poly(lactone) polyols such as poly(caprolactone) diol; polycarboxylic acids such as polyacrylic acid; polyamides such as polyacrylamide and polypeptides; polyamines such as polyethylenimine and polyvinylpyridine; polysulfonic acids or polysulfonates such as poly(sodium-4-styrenesulfonate) and poly(2-acrylamido-methyl-1-propanesulfonic acid; and copolymers thereof (for example, a polypropylene glycol/polyethylene glycol copolymer).

The polymeric densifying agent typically includes repeating units. The repeating unit can be included in the backbone of a compound, such as with a polypeptide, wherein the repeating amide groups occur in the peptide chain. The repeating unit can also refer to units other than backbones, for example, repeating acrylic acid units as in polyacrylic acid.

As used herein, the term "polymer" refers to a macromolecule formed by polymerizing or chemically coupling five or more identical or different monomers; the term "polyamine" refers to a polymer that contains more than one amine functional group; and the term "polyamide" refers to a polymer that contains more than one amide functional group. As noted above, many of the densifying agents include a hydrogen bonding functionality such as, for example, a hydroxyl group, a carboxyl or carboxylate group, a sulfonic acid or sulfonate group, an amide group, an ether group, an amine group or combinations of these groups. By virtue of these functional groups, the polymeric densifying agents can enhance the hydrogen bonding between the fibers and densifying agent; and, for embodiments of the fibrous product that include particles with hydrogen bonding functionality, between the densifying agent and the particles (i.e., to bind particles to the fibers).

The polymeric densifying agents have been found to increase binding efficiency as the length of the polymer increases. The increase in binding efficiency can be attributed to the increased number of hydrogen bonding groups on the polymer with increasing molecular weight.

Although the invention is not limited to polymeric densifying agents of particular molecular weights, polymeric densifying agents having a molecular weight of about 500 grams/mole are preferred because of their attractive physical properties, including being a liquid or an easily handled low melting solid. Polymeric densifying agents with molecular weights greater than about 4,000 grams/mole are less preferred. Polymers with molecular weights between about 4,000 and about 8,000 grams/mole can also be used. However, polymers with molecular weights above 8,000 grams/mole can suffer from decreased binding efficiency because of processing difficulties.

A preferred polymeric densifying agent useful in forming the product of the present invention is a low molecular weight polyethylene glycol (e.g., having a molecular weight from about 500 to about 2,000 grams/mole).

Suitable densifying agents useful in the present invention also include nonpolymeric organic densifying agents. Suitable nonpolymeric organic densifying agents include compounds having at least one functional group capable of forming a hydrogen bond with the fibers. In accordance with the present invention, organic densifying agents can include a functional group selected from a carboxyl or carboxylate group, a carbonyl group, a sulfonic acid or sulfonate group, a phosphoric acid or phosphate group, a hydroxyl group, an amide group, an amine group, and combinations of these groups (e.g., an amino acid or hydroxy acid).

Preferred organic densifying agents include groups that are capable of forming five- or six-membered rings with a functional group on the fiber or, for embodiments that include particles, a functional group on the particle surface. Examples of such groups include amine groups of amino acids and hydroxyl groups of carboxylic acids, alcohols, and amino acids.

Suitable organic densifying agents also include alcohols including primary, secondary, and tertiary alcohols; polyols such as glycols (dihydric alcohols), ethylene glycol, propylene glycol and trimethylene glycol, and triols such as glycerin (1,2,3-propanetriol); other polyols such as sorbitol (i.e., 1,2,3,4,5,6-hexanehexol); amino alcohols such as ethanolamine (2-aminoethanol) and diglycolamine (2-(2-aminoethoxy)ethanol). Other suitable organic densifying agents include nonpolymeric polycarboxylic acids such as citric acid, propane tricarboxylic acid, maleic acid, butanetetracarboxylic acid, cyclopentanetetracarboxylic acid, benzene tetracarboxylic acid, ascorbic acid, tartaric acid, and their salts. Esters of hydroxyl-containing densifying agents can also be used, with mono- and diesters of glycerin, such as monoglycerides and diglycerides, being preferred. Other densifying agents include hydroxy acids such as hydroxyacetic acid, lactic acid, tartaric acid, ascorbic acid, citric acid, and salicylic acid, and their salts; amino acids such as glycine, alanine, valine, serine, threonine, cysteine, glutamic acid, lysine, and β-alanine, asparagine, and glutamine; sulfonic acids and sulfonates; amino-sulfonic acids such as taurine (i.e., 2-aminoethanesulfonic acid); polyamides such as oxamide, urea and biuret; and polyamines such as ethylene diamine and EDTA.

Preferred organic densifying agents include lactic acid, ascorbic acid, citric acid, tartaric acid, and their monovalent cation salts, glycerin, urea and urea derivatives, glycine, β-alanine, mono- and disaccharides, taurine, propylene glycol, dipropyleneglycol, phosphate, phosphoric acid, hydroxy acids and their monovalent cation salts, choline chloride, and combinations thereof. More preferably, the organic densifying agent is selected from glycerin, propylene glycol, sorbitol, lactic acid and its monovalent cation salts, urea, and combinations thereof.

In addition to the polymeric and organic densifying agents described above, suitable densifying agents useful in the present invention include inorganic densifying agents. As with the organic densifying agents, the inorganic densifying agents generally include agents characterized by having a density greater than the density of the dry fibers. When added to the fibers, the inorganic densifying agents increase the fiber mass without appreciably affecting fiber volume. The inorganic densifying agents increase fiber mass without appreciably affecting fiber volume by occupying the preexisting spaces within the fibers, such as the lumen, pores, and the like. Preferably, any increase in fiber volume caused by the addition of the densifying agent is less than the increase in fiber mass, such that the density of the fibers is increased.

Examples of inorganic densifying agents having a density greater than the fibers and that increase the mass of the fibers without appreciably affecting the volume of the fibers include inorganic acid salts in which the cation is monovalent. Monovalent cations include alkali metal, ammonium, or substituted ammonium (such as mono-, di-, tri-, or tetra-alkyl substituted ammonium, with the alkyl groups having from one to six carbon atoms, for example, triethyl or trimethyl ammonium, tetramethyl or tetraethyl ammonium) cations. Suitable densifying agents include alkali metal, ammonium, or substituted ammonium salts of pyrophosphates, hexametaphosphates, tripolyphosphates, hypophosphates, polyphosphoric acid, ethylenediaminetetraacetic acid, hydroxyethylidenediphosphonate; and aminotri(methylenephosphonate). Preferred densifying agents include sodium hypophosphate, tetrapotassium pyrophosphate (TKPP), and tetrasodium pyrophosphate. Other preferred densifying agents include sodium hexametaphosphate, sodium salt of ethylenediaminetetraacetic acid, sodium polyphosphate, sodium salt of diethylenetriaminepentriacetic acid, sodium salt of hydroxyethylethylenediaminetriacetic acid, and sodium salt of dihydroxyethylglycine. Other densifying agents include alkali metal, ammonium, or substituted ammonium salts of oxalates, phosphates, and tungstates. Sodium oxalate, dibasic sodium phosphate, and sodium tungstates are particularly useful. Mixtures of the foregoing densifying agents are also useful.

Suitable densifying agents useful in the present invention also include materials that are hygroscopic in nature yet lack hydrogen bonding sites. When applied to fibers, these materials render the fibers more easily densifiable by drawing moisture into the fibers. Moisture drawn into the fibers provides water that can disrupt intrafiber hydrogen bonding, thereby making the fibers more pliable. Examples of such materials include aluminum halide salts, ammonium halide salts, calcium halide salts, iron halide salts, ammonium acetate, potassium acetate, lithium citrate, and the like. For absorbent articles that include superabsorbent particles, materials having a monovalent cation are preferred.

Preferably, the densifying agent is a combination of densifying agents. In one preferred embodiment, the densifying agent is a mixture of glycerin or propylene glycol, lactic acid, sodium lactate, and optionally sorbitol. In another preferred embodiment, the density agent is a mixture of glycerin or propylene glycol, one or more of the amino acids noted above, and optionally sorbitol.

The densifying agent can be applied to individual fibers, a mass of fibers, or a pulp sheet containing fibers having low coarseness (e.g., juvenile wood fibers) from one or more application devices. Any suitable application device, such as sprayers, roll coaters, immersion applicators, or the like, can be used. Sprayers are typically easier to utilize and incorporate into a pulp sheet manufacturing line. The densifying agent can be applied at various locations or at multiple locations on the pulp sheet manufacturing line including, for example, ahead of the drying stage, intermediate the drying stage, or downstream from the drying stage. For nonaqueous densifying agents, such as glycerin, application to the sheet is preferably downstream from drying.

The fibrous product of the present invention can serve as a source for densifiable fibers, which can be combined with other fibers and materials to provide densifiable fibrous webs and composites. For example, the fibrous product can be transported to a manufacturing line, separated into individual fibers (i.e., fiberized), optionally combined with other fibers or materials, and formed into a fibrous web by air-laid, wet-laid, and foam-forming processes to provide a densifiable fibrous web. The resulting fibrous web, which includes fibers having a coarseness less than about 22 mg/100 m, a densifying agent, and optionally fibers having a coarseness greater than about 22 mg/100 m, can be densified by the external application of pressure to the web (e.g., an airlaid web). The web can be densified by passing it through a set of calender rolls set at a particular pressure (e.g., 60, 90, 150 psi) to provide sheets having increased densities. Densification can also be provided by compaction rolls or presses.

When the densifying agent is applied to a fibrous mass containing fibers having low coarseness (e.g., a blend of juvenile and mature wood fibers), the resulting treated fibers can be densified to a greater extent than fibers that are not treated with a densifying agent. In addition to improving the densification properties of the fibers, preferred densifying agents improved the softness of the fibers in articles containing the fibers. Softness relates to the stiffness of the fibers or articles containing the fibers, the drape or hand of articles including the fibers. Softness also relates to the abrasiveness of a fiber or article containing the fiber. Compressibility is another aspect of softness. Preferred densifying agents that enhance softness include low molecular weight (e.g., from about 500 to about 2000 grams/mole) polyethylene glycol; lactic acid, ascorbic acid, citric acid, tartaric acid, and their monovalent cation salts; glycerin; urea and urea derivatives; glycine; β-alanine; mono- and disaccharides; taurine; propylene glycol; dipropyleneglycol; phosphate; phosphoric acid; hydroxy acids and their monovalent cation salts; choline chloride; sodium hypophosphate; tetrapotassium pyrophosphate (TKPP); tetrasodium pyrophosphate; sodium hexametaphosphate; sodium salt of ethylenediaminetetraacetic acid; sodium polyphosphate; sodium salt of diethylenetriaminepentriacetic acid; sodium salt of hydroxyethylethylenediaminetriacetic acid; sodium salt of dihydroxyethylglycine; alkali metal, ammonium, or substituted ammonium salts of oxalates, phosphates, and tungstates; ammonium halide salts; lithium citrate; and potassium acetate.

Without intending to be bound by the following theory, one explanation for the effect of the densifying agents on the densification and softness of the fibers relates to the hydrogen bonding that occurs between cellulose molecules within a cellulose fiber and within a specific cellulose molecule. When applied to the fibers, the densifying agents can disrupt, or promote the disruption of, existing hydrogen bonding between cellulose molecules or within a given cellulose molecule. The densifying agent can occupy hydrogen bonding sites on the cellulose molecule, thereby preventing hydrogen bonding that would otherwise occur within the molecule or with other cellulose molecules. Alternatively, the densifying agent, while itself not disrupting intermolecular and intramolecular hydrogen binding, can draw into the fibers other hydrogen bonding disruptors, such as atmospheric moisture, thereby effecting the fibers' hydrogen bonding.

As noted above, the present invention provides a fibrous product that includes fibers having low coarseness (e.g., juvenile wood fibers) and a densifying agent. When densified, the fibrous product of the invention attains a higher density than either of its component fibrous materials or the component fibrous materials treated with an equivalent amount of densifying agent. Handsheets were formed by conventional forming methods incorporating the fibers and densifying agents as indicated. A representative fibrous product of the invention was formed from a 30:70 blend of low coarseness (i.e., juvenile) and mature wood fibers (NB416) and included about 3 percent by weight of a 70:30 blend of sorbitol and propylene glycol as the densifying agent. The handsheets were then fiberized and airlaid to form a bulky fibrous matrix, which was then compressed and the density of the resulting products measured.

A comparison of the densification of fibrous airlaid webs formed from these materials is summarized in Table 1 below.

TABLE 1

Densification Results

| Handsheet Composition | Density (g/cc) |
|---|---|
| NB416 | 0.253 |
| Tops | 0.252 |
| Blend 30/70 (Tops/NB416) | 0.253 |
| NB416 (3% treated) | 0.291 |
| Tops (3% treated) | 0.302 |
| Blend 30/70 (Tops/NB416, 3% treated) | 0.356 |
| NB416 (9% treated) | 0.285 |
| Tops (9% treated) | 0.331 |

As shown in Table 1, densification at 150 psi of airlaid webs prepared from southern bleached kraft fluff pulp (available from Weyerhaeuser Company under the designation NB416), low coarseness (i.e., juvenile wood) fibers obtained from treetops (Tops), and a 30:70 blend of low coarseness fibers from treetops and NB416 (Blend 30/70) provided airlaid webs having approximately the same density (i.e., 0.253 g/cc). Identically formed handsheets were treated with 3 percent by weight based on total weight of fibers of a 70:30 blend of sorbitol and propylene glycol as the densifying agent. These handsheets were fiberized and the resulting fibers airlaid and densified at 150 psi. The airlaid web formed from low coarseness fibers and treated with the densifying agent had a slightly higher density (i.e., 0.302 g/cc) than the airlaid webs formed from mature fibers and treated with the same amount of densifying agent (i.e., 0.291 g/cc). A significant and unexpected increase in density was observed for airlaid webs formed from a 30:70 blend of low coarseness and mature wood fibers treated with 3 percent of the sorbitol/propylene glycol (70:30) densifying agent. The density of the airlaid webs (0.356 g/cc) represents an increase in density of about 20 percent relative to either of the fibrous components alone treated with a densifying agent. The enhanced density of the fibrous product including low coarseness and mature wood fibers and densifying agent was also significantly greater than for either of the airlaid webs prepared from juvenile and mature wood fibers alone treated with about 9 percent densifying agent. Some commercially available pulp sheets include about 9 percent densifying agent. Accordingly, the present invention provides an improved, densified fibrous product that includes only about one-third the amount of the relatively expensive densifying agent. The result is that the fibrous product of the present invention can be prepared at lower cost and uses a previously underutilized forest resource.

In addition to providing a fibrous product that can be readily densified, the fibrous product of the present invention can be readily fiberized. The fiberization energy required to reduce the handsheets prepared as described above to individualized fibers was determined using a laboratory scale hammermill (Kamas Hammermill, Kamas Industri AB, Sweden). Briefly, pulp samples were placed in a 50-percent-humidity room for a minimum of about four hours prior to fiberization. Pulp samples consisted of sheet strips weighing at least about 150 grams. For each sample, the pulp strip was fed into the fiberizer's feed port such that at least about 145 grams of fluff were produced for each sample sheet. The fiberized weight for each sample was determined by subtracting the weight of the residual sheet (i.e., the portion of the sheet not fed into the fiberizer) from the initial sheet weight. The energy required to fiberize each pulp sheet was measured by the hammermill and displayed on its energy digital readout in units of watt hours (wM). Fiberization energy was then calculated for each pulp sheet using the following equation:

Fiberization energy (kJ/kg)=3,600×energy (wH)/fiberized weight (g).

The fiberization energy results are summarized in Table 2 below.

TABLE 2

Fiberization Energy Results

| Handsheet Composition | Fiberization Energy (kJ/kg) |
| --- | --- |
| NB416 | 155 |
| Tops | 182 |
| Blend 30/70 (Tops/NB416) | 150 |
| NB416 (3% treated) | 146 |
| Tops (3% treated) | 170 |
| Blend 30/70 (Tops/NB416, 3% treated) | 144 |
| NB416 (9% treated) | 141 |
| Tops (9% treated) | 155 |

As indicated in Table 2, fibrous handsheets prepared from low coarseness (i.e., juvenile wood) fibers are fiberized with difficulty. Even when treated with the densifying agent useful in the present invention, the energy required to separate the fibrous handsheet into individual fibers decreases only slightly (e.g., 182 kJ/kg for untreated, 170 kJ/kg for 3 percent treated, and 155 kJ/kg for 9 percent treated). Mature wood fibers are more readily fiberized (e.g., 155 kJ/kg for untreated NB416, 146 kJ/kg for 3 percent treated NB416, and 141 kJ/kg for 9 percent treated NB416). While the 30:70 blend of low coarseness and mature wood fibers provided a handsheet that required less energy to fiberize relative to the corresponding handsheet prepared from mature wood fibers, the same blend that included 3 percent densifying agent was more readily fiberized. The fiberization energy required for the 3 percent treated 30:70 blend is comparable to the energy required to fiberize currently commercially available pulp sheets (e.g., 9 percent treated NB416).

The liquid absorption properties for handsheets prepared as described above was determined using a Weyerhaeuser Fluff Absorbency Quality (FAQ) Tester. In the test, 4.0 grams of the fiberized material were airlaid into a cylinder having a liquid pervious bottom. The cylinder containing the fluff was then placed into a well and a metal foot applied a load of 0.6 kPa to the fluff and its bulk was calculated. An additional weight was then added to the foot to increase the applied pressure to 2.5 kPa and bulk was again calculated (see Dry Bulk in Table 5). Water was then contacted with the bottom of the cylinder and the time required for establishment of an electrical connection between the water at the bottom of the container and the metal foot at the top of the fluff was measured (i.e., absorption time). Based on the absorption time and the bulk of the sample, the absorption rate was then calculated (see Table 3). The bulk of the wet mass of fibers was calculated (see Wet Bulk in Table 5), the amount of water absorbed by the fluff measured, and the capacity of the fluff calculated (see Table 4).

The absorption time and absorption rate for the handsheets is summarized in Table 3.

TABLE 3

Absorption Properties

| Handsheet Composition | Absorption Time(s) | Rate (mm/s) |
| --- | --- | --- |
| NB416 | 2.9 | 30 |
| Tops | 3.4 | 25 |
| Blend 30/70 (Tops/NB4l6) | 3.0 | 29 |
| NB416 (3% treated) | 2.5 | 33 |
| Tops (3% treated) | 2.7 | 27 |
| Blend 30/70 (Tops/NB416, 3% treated) | 2.3 | 31 |
| NB416 (9% treated) | 2.1 | 35 |
| Tops (9% treated) | 2.4 | 28 |

As indicated in Table 3, airlaid webs formed from low coarseness fibers are less absorptive than corresponding airlaid webs formed from mature wood fibers. Airlaid webs formed from low coarseness fibers exhibit greater liquid absorption times and lower liquid absorption rates compared to airlaid webs formed from mature wood fibers. Increasing the amount of densifying agent for either mature or low coarseness fiber airlaid webs enhanced the airlaid webs' absorbence, decreasing absorption time and increasing absorption rate. For the airlaid web formed from the 30:70 blend of low coarseness and mature wood fibers, the inclusion of densifying agent significantly reduced the absorption time (i.e., from about 3.0 seconds to about 2.3 seconds) and also increased the absorbence rate from about 29 to about 31 mm/second. The absorption time for the treated 30:70 blend was slightly greater than that of the commercially available pulp sheet, and the blend's absorption rate was also slightly less than the commercially available pulp sheet.

The fluff capacity, defined as grams of water retained per gram fibers, was determined from fibers obtained from the handsheets prepared as described above. The fluff capacity results are summarized in Table 4.

TABLE 4

Fluff Capacity

| Pulp | Capacity (g/g) |
| --- | --- |
| NB416 | 11.5 |
| Tops | 12.3 |
| Blend 30/70 (Tops/NB416) | 12.0 |
| NB416(3% treated) | 11.2 |
| Tops (3% treated) | 11.7 |

TABLE 4-continued

Fluff Capacity

| Pulp | Capacity (g/g) |
| --- | --- |
| Blend 30/70 (Tops/NB416, 3% treated) | 10.6 |
| NB416 (9% treated) | 10.5 |
| Tops (9% treated) | 10.9 |

Generally, the capacity of low coarseness fibers is greater than mature wood fibers and increasing the amount of densifying agent reduces the capacity for both low coarseness and mature wood fibers. For the 30:70 blend of low coarseness fibers and mature wood fibers, the addition of 3 percent densifying agent provided fibers having a fluff capacity slightly greater than commercially available fibers having a significantly greater amount of densifying agent.

The fluff bulk of fibers obtained from the handsheets described above was also determined. Dry and wet bulks at 0.6 kPa and 2.5 kPa were determined. The fluff bulk results are summarized in Table 5.

TABLE 5

Fluff Bulk

| | Dry Bulk (cc/g) | | Wet Bulk cc/g | |
| --- | --- | --- | --- | --- |
| Pulp | 0.6 kPa | 2.5 kPa | 0.6 kPa | 2.5 kPa |
| NB416 | 54 | 26 | 11 | 10 |
| Tops | 51 | 26 | 12 | 11 |
| Blend 30/70 (Tops/NB416) | 57 | 27 | 12 | 11 |
| NB416 (3% treated) | 52 | 25 | 10 | 10 |
| Tops (3% treated) | 47 | 24 | 11 | 10 |
| Blend 30/70 (Tops/NB416, 3% treated) | 45 | 23 | 10 | 9 |
| NB416 (9% treated) | 46 | 23 | 10 | 9 |
| Tops (9% treated) | 44 | 23 | 10 | 9 |

As noted above for fluff capacity, fluff bulk for the fibers obtained from a handsheet formed from 30:70 blend of low coarseness and mature wood fibers having 3 percent densifying agent was determined to be comparable to the presently commercially available material.

In another embodiment, the present invention provides a highly compressible wood pulp product that includes wood fibers having low coarseness, preferably juvenile wood fibers, and a densifying agent. For these products, suitable fibers and densifying agents include those described above. In this embodiment, the densifying agent is present in the product in an amount from about 0.1 to about 15 percent by weight, preferably from about 0.5 to about 10 percent by weight, and more preferably from about 0.7 to about 9 percent by weight based on the total weight of the product. In one preferred embodiment, the densifying agent is present in about 4.5 percent by weight of the total product.

As for the highly compressible product described above that includes fibers having low coarseness and fibers having high coarseness (e.g., a blend of juvenile and mature wood fibers), the product including low coarseness fibers and densifying agent is also highly compressible and provides a highly densified product that is readily fiberized. The properties of a representative product of the invention, a handsheet formed from juvenile wood obtained from 7.5-year-old treetops from mature 28-year-old southern pine trees (Tops), are compared to those of corresponding handsheets formed from mature wood fibers (mature southern pine designated PD416 and NB416) in Table 6. For these products, the densifying agent was a 70:30 blend of sorbitol and propylene glycol.

TABLE 6

Density and Fiberization Energy

| Pulp | Densifying Agent (%) | Coarseness (mg/100 m) | Densification (gm/cc) | | | Energy (kJ/kg) |
| --- | --- | --- | --- | --- | --- | --- |
| | | | 50 psi | 100 psi | 150 psi | |
| PD416 | 4.5 | — | 0.128 | 0.193 | 0.269 | 89 |
| NB416 | 4.5 | — | 0.132 | 0.227 | 0.277 | 133 |
| Top | 4.5 | 18.4 | 0.104 | 0.229 | 0.354 | 103 |

As shown in Table 6, the density achieved for the compressible product of the invention was significantly greater than for either of the corresponding products formed from mature fibers including the same amount of densifying agent. The density of the product formed from low coarseness fibers (densification at 150 psi) was more than 20 percent greater than that of the products formed from mature fibers (i.e., 22 percent greater than for PD416 and 24 percent greater than for NB416). Furthermore, the representative product was also readily fiberized.

To summarize, in one aspect, the present invention provides an improved, densified fibrous product that includes only a fraction of the relatively expensive densifying agent. Thus, the fibrous product of the present invention uses a previously underutilized forest resource and can be prepared at lower cost than the presently commercially available materials. Furthermore, the fibrous product is readily fiberized and has liquid absorption properties substantially equivalent to comparable commercially available materials that include significantly greater amounts of chemical additives.

As described above, wood fibers having low coarseness, preferably obtained from juvenile wood fibers (e.g., from treetops and thinnings) can advantageously substitute for densifying agents providing softness and flexibility as well as enhancing bonding in fibrous sheets. In addition, wood fibers having low coarseness, such as juvenile wood fibers, can also be incorporated into tissue and toweling products to provide a high bonding, elastic, and soft component for tissue products. Wood fibers having low coarseness can also be useful as high-performance, nonchemical absorbents and as such can be useful as liquid management, acquisition, distribution, or storage layers in consumer absorbent products. In addition, these fibers can be useful as fluff for high capacity, superabsorbent polymer composites.

In one aspect, the present invention provides a fibrous product that is a densifiable fibrous composite (i.e., a compressible composition) that includes, in one embodiment, fibers having low coarseness and a densifying agent, and in another embodiment, fibers having relatively greater coarseness, fibers having low coarseness, and a densifying agent. In another aspect, the present invention provides a densified product formed by compacting a fibrous web that includes fibers having low coarseness, a densifying agent, and, optionally, fibers having relatively greater coarseness. To further enhance the absorbent properties of either the compressible composition or the densified product, each can further include absorbent material, such as a superabsorbent polymeric material. As noted above, absorbent material in the form of superabsorbent polymer particles can be advantageously affixed to the fibrous composites of the invention through the densifying agent.

As used herein, the term "absorbent material" refers to a material that absorbs liquid and that generally has an absorbent capacity greater than the cellulosic fibrous component of the composite. Preferably, the absorbent material is a water-swellable, generally water-insoluble polymeric material capable of absorbing at least about 5, desirably about 20, and preferably about 100 times or more its weight in saline (e.g., 0.9 percent saline). The absorbent material can be swellable in the dispersion medium utilized in the method for forming the composite. In one embodiment, the absorbent material is untreated and swellable in the dispersion medium. In another embodiment, the absorbent material is a coated absorbent material that is resistant to absorbing water during the composite formation process.

The amount of absorbent material present in the composite can vary greatly depending on the composite's intended use. The absorbent material is suitably present in the composite in an amount from about 5 to about 60 weight percent, preferably from about 30 to about 50 weight percent, based on the total weight of the composite.

The absorbent material may include natural materials such as agar, pectin, and guar gum, and synthetic materials, such as synthetic hydrogel polymers. Synthetic hydrogel polymers include, for example, carboxymethyl cellulose, alkaline metal salts of polyacrylic acid, polyacrylamides, polyvinyl alcohol, ethylene maleic anhydride copolymers, polyvinyl ethers, hydroxypropyl cellulose, polyvinyl morpholinone, polymers and copolymers of vinyl sulphonic acid, polyacrylates, polyacrylamides, and polyvinyl pyridine among others. In a preferred embodiment, the absorbent material is a superabsorbent material. As used herein, a "superabsorbent material" refers to a polymeric material that is capable of absorbing large quantities of fluid by swelling and forming a hydrated gel (i.e., a hydrogel). In addition to absorbing large quantities of fluids, superabsorbent materials can also retain significant amounts of bodily fluids under moderate pressure.

Superabsorbent materials generally fall into three classes: starch graft copolymers, crosslinked carboxymethylcellulose derivatives, and modified hydrophilic polyacrylates. Examples of such absorbent polymers include hydrolyzed starch-acrylonitrile graft copolymers, neutralized starch-acrylic acid graft copolymers, saponified acrylic acid ester-vinyl acetate copolymers, hydrolyzed acrylonitrile copolymers or acrylamide copolymers, modified crosslinked polyvinyl alcohol, neutralized self-crosslinking polyacrylic acids, crosslinked polyacrylate salts, carboxylated cellulose, and neutralized crosslinked isobutylene-maleic anhydride copolymers.

Superabsorbent materials are available commercially, for example, polyacrylates from Stockhausen, Greensboro, N.C. These superabsorbent polymers come in a variety of sizes, morphologies, and absorbent properties (available from Clariant under trade designations such as IM 3500 and IM 3900). Other superabsorbent materials are marketed under the trademarks SANWET (supplied by Sanyo Kasei Kogyo Kabushiki Kaisha), and SXM77 (supplied by Stockhausen of Greensboro, N.C.). Other superabsorbent materials are described in U.S. Pat. No. 4,160,059; U.S. Pat. No. 4,676,784; U.S. Pat. No. 4,673,402; U.S. Pat. No. 5,002,814; U.S. Pat. No. 5,057,166; U.S. Pat. No. 4,102,340; and U.S. Pat. No. 4,818,598, all expressly incorporated herein by reference. Products such as diapers that incorporate superabsorbent materials are described in U.S. Pat. No. 3,699,103 and U.S. Pat. No. 3,670,731.

Suitable superabsorbent materials useful in the absorbent composite of the present invention include superabsorbent particles and superabsorbent fibers.

In a preferred embodiment, the absorbent composite of the present invention includes superabsorbent material that swells relatively slowly for the purposes of composite manufacturing and yet swells at an acceptable rate so as not to adversely affect the absorbent characteristics of the composite or any construct containing the composite. Generally, the smaller the absorbent material, the more rapidly the material absorbs liquid.

The composites of the present invention can be used in the formation of absorbent articles. The composites can be directly incorporated into an absorbent article such as, for example, a diaper or feminine care product. Alternatively, the composites can serve as a source of highly densifiable fibers and can be separated into individual fibers (i.e., fiberized), optionally combined with other fibers and/or materials, and formed into fibrous webs by air-laid, wet-laid, or foam-forming methods to provide densifiable composites that can be incorporated into absorbent articles. For the purposes of the following discussion relating to absorbent constructs and articles, reference numeral 10 refers to an absorbent composite that is either a densifiable or densified composite that includes fibers having a coarseness less than about 22 mg/100 m, a densifying agent, and optionally fibers having a coarseness greater than about 22 mg/100 m. As described above, the composite can also include other fibers and materials including, for example, synthetic fibers, crosslinked fibers, and superabsorbent particles.

Figure 2:
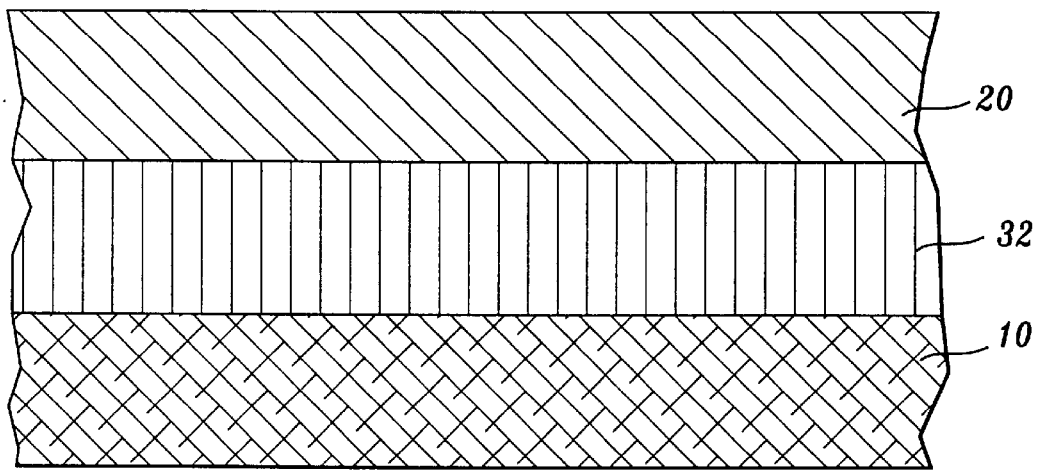
FIG. 2 is a cross-sectional view of a portion of another absorbent construct incorporating a composite formed in accordance with the present invention, an acquisition/distribution layer, and an intermediate layer.

The composite can be used alone or, as illustrated in FIGS. 1 and 2, can be used in combination with one or more other layers. In FIG. 1, absorbent composite 10 is employed as a storage layer in combination with upper acquisition layer 20. As illustrated in FIG. 2, a third layer 32 (e.g., distribution layer) can also be employed, if desired, with absorbent composite 10 and acquisition layer 20.

Figure 3:
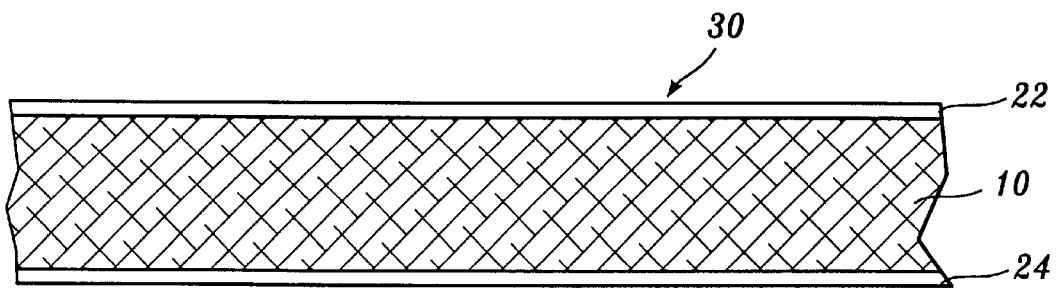
FIG. 3 is a cross-sectional view of a portion of an absorbent article incorporating a composite formed in accordance with the present invention.

A variety of suitable absorbent articles can be produced from the absorbent composite. The most common include absorptive consumer products, such as diapers, feminine hygiene products such as feminine napkins, and adult incontinence products. As noted above, the composite can be incorporated into an absorbent article by combining the composite with facing and backing sheets. Referring to FIG. 3, one representative absorbent article includes absorbent composite 10 interposed between liquid pervious facing sheet 22 and liquid impervious backing sheet 24. Absorbent article can also be formed by combining the composite of the invention with other layers including acquisition, distribution, and storage layers. For example, referring to FIG. 4, absorbent article 40 comprises absorbent composite 10 and overlying acquisition layer 20. Liquid pervious facing sheet 22 overlies acquisition composite 20, and liquid impervious backing sheet 24 underlies absorbent composite 10. In the absorbent articles described above, the facing sheet is joined to the backing sheet. The absorbent composite will provide advantageous liquid absorption performance for use in, for example, diapers. The absorbent composite will aid in fluid transport and absorption in multiple wettings. For absorbent articles that incorporate the composite of the invention and that are suitable for use as diapers or as incontinence products, the articles can further include leg gathers.

Figure 4:
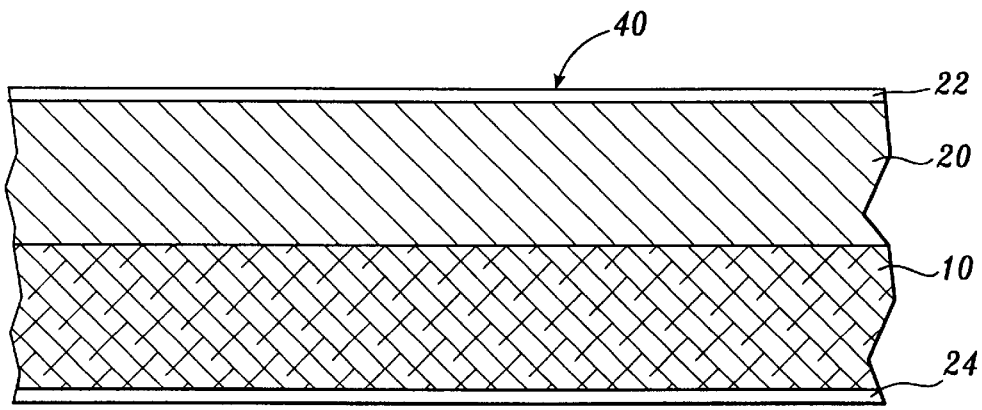
FIG. 4 is a cross-sectional view of a portion of an absorbent article incorporating a composite formed in accordance with the present invention and an acquisition/distribution layer.
Figure 5:
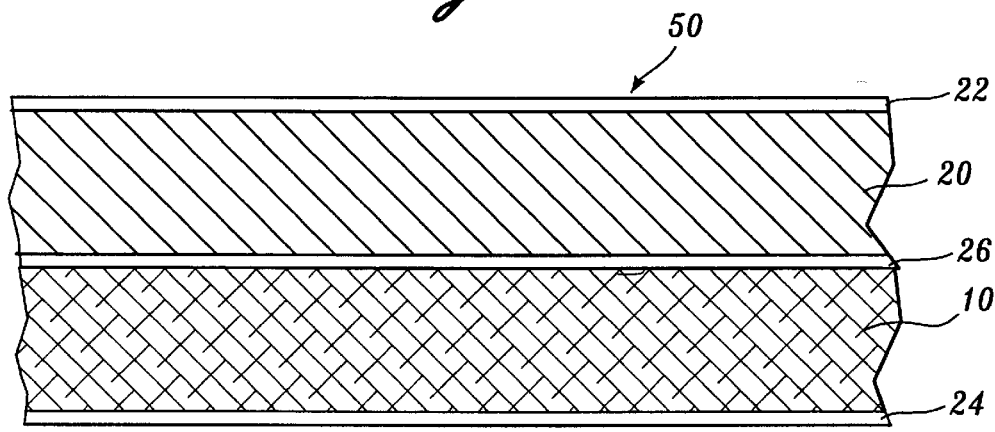
FIG. 5 is a cross-sectional view of a portion of another absorbent article incorporating a composite formed in accordance with the present invention, an acquisition/distribution layer, and an intermediate layer.

The constructs in FIGS. 3 and 4 are shown for purposes of exemplifying typical absorbent articles, such as a diaper or feminine napkin. One of ordinary skill will be able to make a variety of different constructs using the concepts taught herein. The example, a typical construction of an adult incontinence absorbent structure is shown in FIG. 5. Article 50 comprises facing sheet 22, acquisition layer 20, absorbent composite 10, and backing sheet 24. Facing sheet 22 is pervious to liquid while backing sheet 24 is impervious to liquid. In these articles, the facing sheet is joined to the backing sheet. In this construct, liquid pervious tissue 26 composed of a polar, fibrous material is positioned between absorbent composite 10 and acquisition layer 20.

Figure 6:
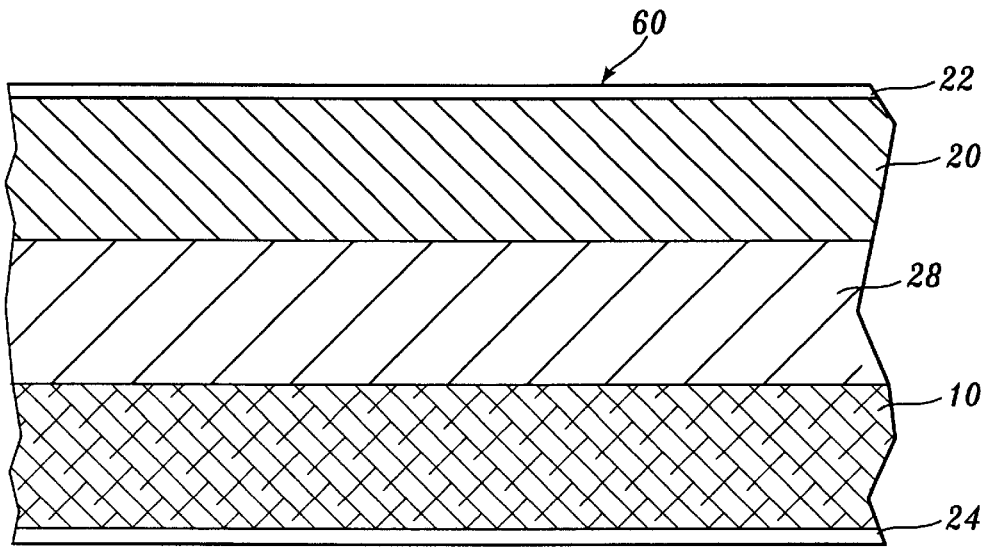
FIG. 6 is a cross-sectional view of a portion of another absorbent article incorporating a composite formed in accordance with the present invention, an acquisition/distribution layer, and an intermediate layer.

Referring to FIG. 6, another absorbent article includes facing sheet 22, acquisition layer 20, intermediate layer 28, absorbent composite 10, and backing sheet 24 (facing and backing sheet being joined together). Intermediate layer 28 contains, for example, a densified fibrous material such as a combination of cellulose acetate and triacetin, which are combined prior to forming the article. Intermediate layer 28 can thus bond to both absorbent composite 10 and acquisition layer 20 to form an absorbent article having significantly more integrity than one in which the absorbent composite and acquisition layer are not bonded to each other. The hydrophilicity of layer 28 can be adjusted in such a way as to create a hydrophilicity gradient among layers 10, 28, and 20.

Figure 7:
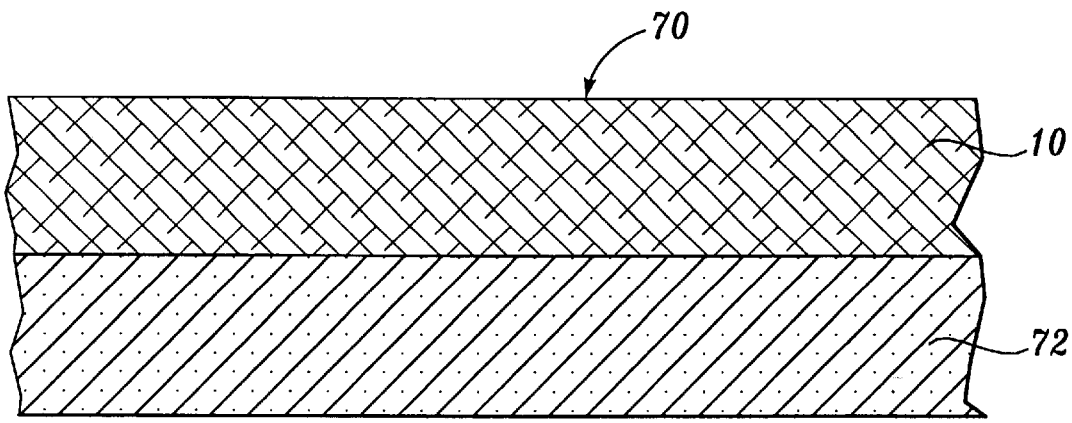
FIG. 7 is a cross-sectional view of a portion of an absorbent construct incorporating a composite formed in accordance with the present invention and a storage layer.
Figure 8:
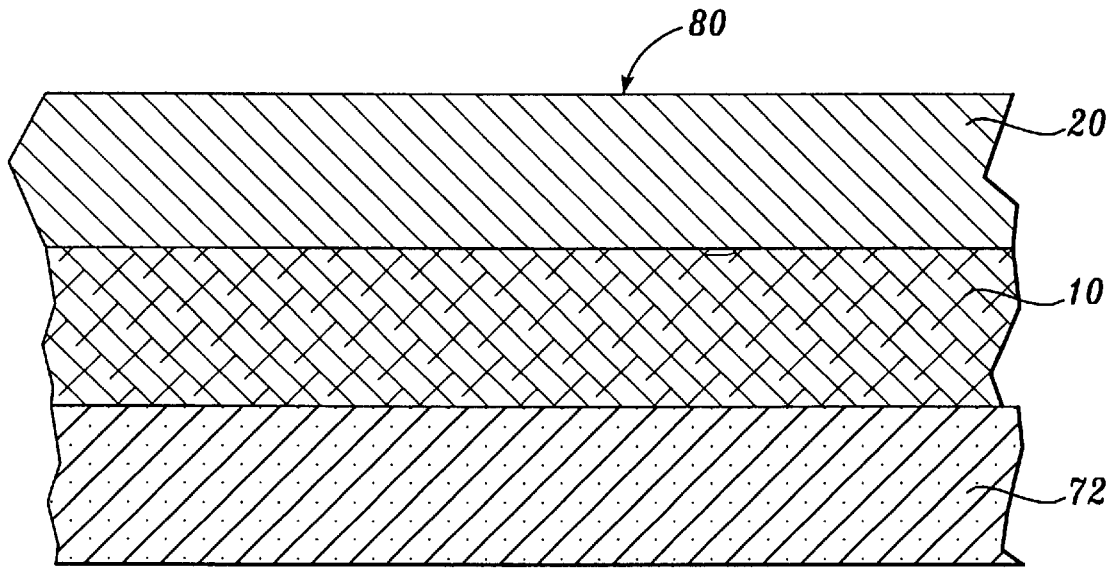
FIG. 8 is a cross-sectional view of a portion of another absorbent construct incorporating a composite formed in accordance with the present invention, an acquisition/distribution layer, and a storage layer.

The composite of the invention can also be incorporated as a liquid management layer in an absorbent article such as a diaper. In such an article, the composite can be used in combination with a storage core or layer. In the combination, the liquid management layer can have a top surface area that is smaller, the same size, or greater than the top surface area of the storage layer. Representative absorbent constructs that incorporate the composite in combination with a storage layer are shown in FIGS. 7 and 8. Referring to FIG. 7, absorbent construct 70 includes composite 10 and storage layer 72. Storage layer 72 is preferably a fibrous layer that includes absorbent material. The storage layer can be formed by any method including air-laid, wet-laid, and foam-forming methods.

Figure 9:
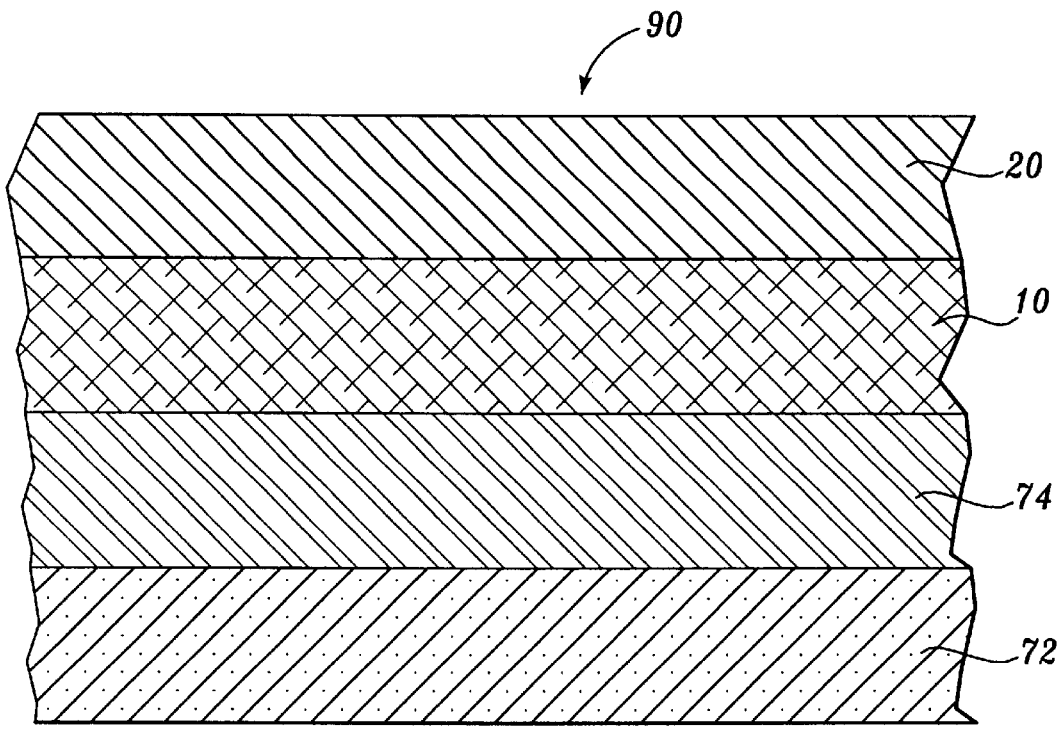
FIG. 9 is a cross-sectional view of a portion of another absorbent construct incorporating a composite formed in accordance with the present invention, an acquisition/distribution layer, an intermediate layer, and a storage layer.

An acquisition layer can be combined with the composite and storage layer. FIG. 8 illustrates absorbent construct 80 having acquisition layer 20 overlying composite 10 and storage layer 72. Construct 80 can further include intermediate layer 74 to provide construct 90 shown in FIG. 9. Intermediate layer 74 can be, for example, a tissue layer, a nonwoven layer, an air-laid or wet-laid pad, or a fibrous composite of the invention.

Figure 10:
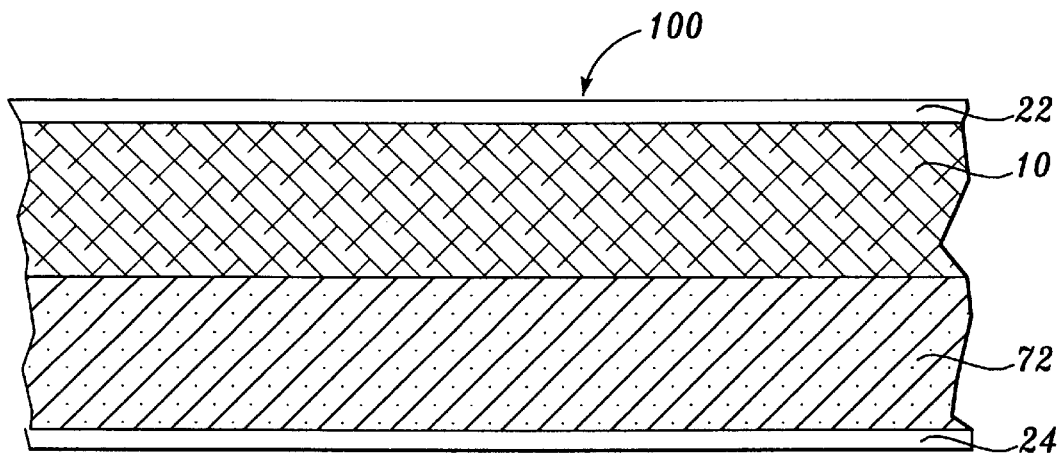
FIG. 10 is a cross-sectional view of a portion of an absorbent article incorporating a composite formed in accordance with the present invention and a storage layer.
Figure 11:
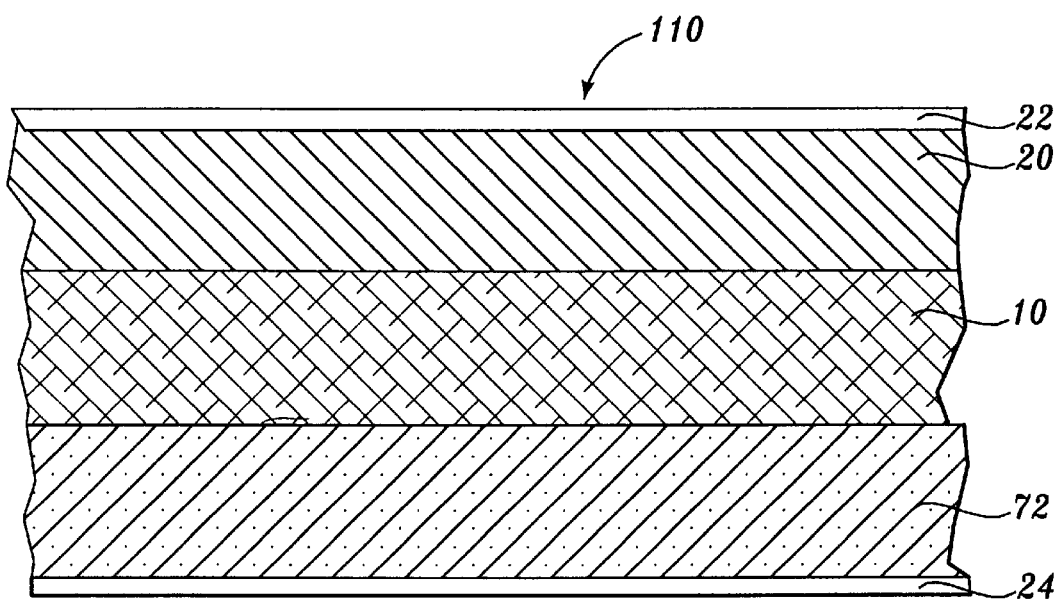
FIG. 11 is a cross-sectional view of a portion of another absorbent article incorporating a composite formed in accordance with the present invention, an acquisition/distribution layer, and a storage layer.
Figure 12:
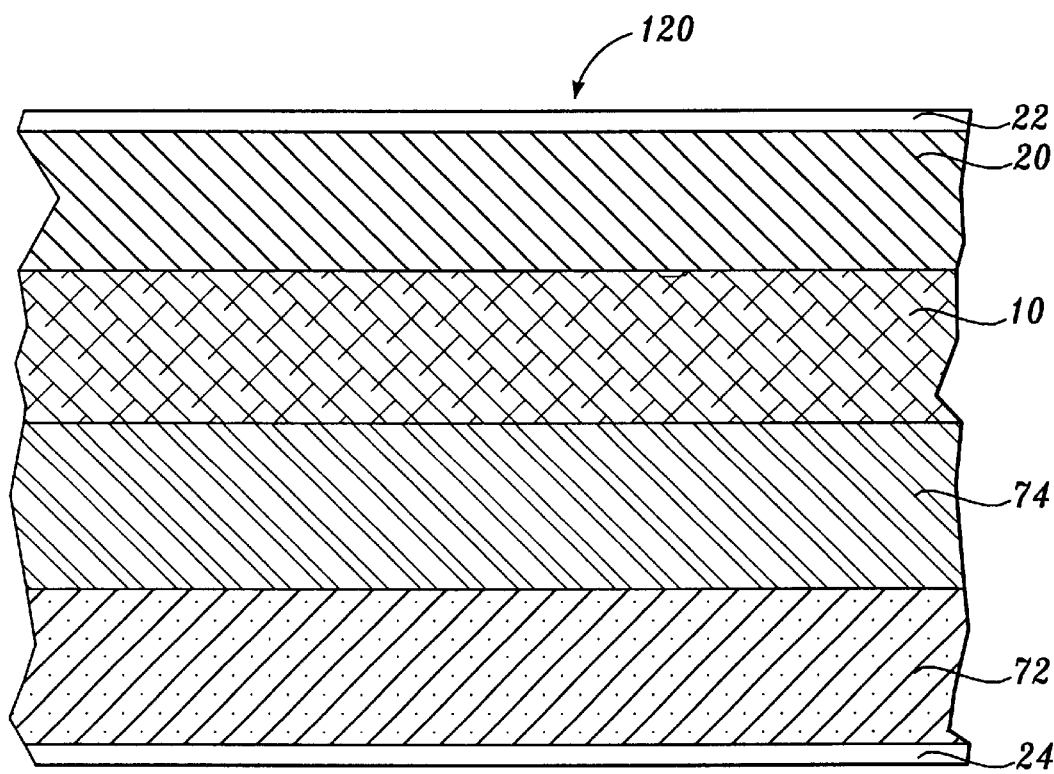
FIG. 12 is a cross-sectional view of a portion of another absorbent article incorporating a composite formed in accordance with the present invention, an acquisition/distribution layer, an intermediate layer, and a storage layer.

Constructs 70, 80, and 90 can be incorporated into absorbent articles. Generally, absorbent articles 100, 110, and 120, shown in FIGS. 10–12, respectively, include liquid pervious facing sheet 22, liquid impervious backing sheet 24, and constructs 70, 80, and 90, respectively. In such absorbent articles, the facing sheet is joined to the backing sheet.

While the preferred embodiment of the invention has been illustrated and described, it will be appreciated that various changes can be made therein without departing from the spirit and scope of the invention.

The embodiments of the invention in which an exclusive property or privilege is claimed are defined as follows:

1. A wood pulp composition comprising wood fibers having a fiber coarseness less than about 22 mg/100 m and a densifying agent.

2. The composition of claim 1 wherein the wood fibers have a coarseness less than about 20 mg/100 m.

3. The composition of claim 1 wherein the wood fibers have a coarseness in the range from about 7 to about 18 mg/100 m.

4. The composition of claim 1 wherein the wood fibers comprise juvenile wood pulp fibers.

5. The composition of claim 1 wherein the densifying agent is present from about 0.1 to about 15 percent by weight based on the total weight of the composition.

6. The composition of claim 5 further comprising wood fibers having a fiber coarseness greater than about 22 mg/100 m.

7. The composition of claim 1 wherein the densifying agent is present from about 0.7 to about 9 percent by weight based on the total weight of the composition.

8. The composition of claim 1 wherein the densifying agent is present in about 4.5 percent by weight based on the total weight of the composition.

9. The composition of claim 1 wherein the wood fibers comprise wood fibers obtained from treetops.

10. The composition of claim 1 wherein the wood fibers comprise wood fibers obtained from tree thinnings.

11. The composition of claim 1 wherein the densifying agent is selected from the group consisting of a polymeric densifying agent, an organic densifying agent, an inorganic densifying agent, and mixtures thereof.

12. The composition of claim 11 wherein the polymeric densifying agent is selected from the group consisting of a polyglycol, a polycarboxylic acid, a polyamide, a polyamine, and mixtures thereof.

13. The composition of claim 11 wherein the organic densifying agent is selected from the group consisting of a polyol, a carboxylic acid, a carboxylic acid salt, an amide, and mixtures thereof.

14. The composition of claim 13 wherein the polyol is selected from the group consisting of an ethylene glycol, propylene glycol, sorbitol, glycerin, and mixtures thereof.

15. The composition of claim 13 wherein the carboxylic acid is selected from the group consisting of a citric acid, ascorbic acid, maleic acid, lactic acid, and mixtures thereof.

16. The composition of claim 13 wherein the carboxylic acid salt comprises sodium lactate.

17. The composition of claim 13 wherein the carboxylic acid comprises an amino acid.

18. The composition of claim 17 wherein the amino acid is selected from the group consisting of glycine and β-alanine.

19. The composition of claim 13 wherein the amide is selected from the group consisting of urea, urea derivatives, and mixtures thereof.

20. The composition of claim 1 wherein the densifying agent comprises a blend of sorbitol and propylene glycol.

21. The composition of claim 1 wherein the densifying agent comprises a hygroscopic material.

22. The composition of claim 21 wherein the hygroscopic material is selected from the group consisting of halide salts of ammonium, aluminum, calcium, and iron; ammonium acetate; potassium acetate; and lithium citrate.

23. The composition of claim 1 further comprising superabsorbent material.

24. A compressible wood pulp composition formed by applying a densifying agent to wood fibers having a fiber coarseness less than about 22 mg/100 m.

25. The composition of claim 24 further comprising superabsorbent material.

26. The composition of claim 24 further comprising wood fibers having a fiber coarseness greater than about 22 mg/100 m.

27. The composition of claim 26 further comprising superabsorbent material.

28. A densified pulp product formed by compacting a fibrous web comprising a densifying agent and wood fibers having a fiber coarseness less than about 22 mg/100 m.

29. The composition of claim 28 further comprising superabsorbent material.

30. The product of claim 28 further comprising wood fibers having a fiber coarseness greater than about 22 mg/100 m.

31. The composition of claim 30 further comprising superabsorbent material.

32. An absorbent article comprising a wood pulp composition comprising wood fibers having a fiber coarseness less than about 22 mg/100 m and a densifying agent.

33. The absorbent article of claim 32 wherein the article is a diaper.

34. The absorbent article of claim 32 wherein the article is a feminine care product.

35. The absorbent article of claim 32 wherein the article is an adult incontinence product.

36. The absorbent article of claim 32 wherein the wood pulp composition further comprises superabsorbent material.

37. An absorbent article comprising a compressible wood pulp composition formed by applying a densifying agent to wood fibers having a fiber coarseness less than about 22 mg/100 m.

38. The absorbent article of claim 37 wherein the wood pulp composition further comprises superabsorbent material.

39. An absorbent article comprising a densified pulp product formed by compacting a fibrous web comprising a densifying agent and wood fibers having a fiber coarseness less than about 22 mg/100 m.

40. The absorbent article of claim 39 wherein the wood pulp composition further comprises superabsorbent material.

41. The composition of claim 1 further comprising wood fibers having a fiber coarseness greater than about 22 mg/100 m.

42. The composition of claim 41 wherein the wood fibers having a fiber coarseness greater than about 22 mg/100 m comprise mature wood fibers.

43. The composition of claim 41 wherein the wood fibers having a fiber coarseness greater than about 22 mg/100 m comprise southern pine fibers.

44. The composition of claim 41 wherein the wood fibers having a fiber coarseness less than about 22 mg/100 m are present from about 10 to about 50 percent by weight based on the total weight of the composition.

45. The composition of claim 41 wherein the wood fibers having a fiber coarseness less than about 22 mg/100 m are present in about 30 percent by weight based on the total weight of the composition.

46. The composition of claim 41 wherein the densifying agent is present from about 0.1 to about 15 percent by weight based on the total weight of the composition.

47. The composition of claim 41 wherein the densifying agent is present from about 0.7 to about 9 percent by weight based on the total weight of the composition.

48. The composition of claim 41 wherein the densifying agent is present in about 3 percent by weight based on the total weight of the composition.

49. The composition of claim 41 wherein the densifying agent is selected from the group consisting of a polymeric densifying agent, an organic densifying agent, an inorganic densifying agent, and mixtures thereof.

50. The composition of claim 49 wherein the polymeric densifying agent is selected from the group consisting of a polyglycol, a polycarboxylic acid, a polyamide, a polyamine, and mixtures thereof.

51. The composition of claim 49 wherein the organic densifying agent is a selected from the group consisting of a polyol, a carboxylic acid, a carboxylic acid salt, an amide, and mixtures thereof.

52. The composition of claim 51 wherein the polyol is selected from the group consisting of ethylene glycol, propylene glycol, sorbitol, glycerin, and mixtures thereof.

53. The composition of claim 51 wherein the carboxylic acid is selected from the group consisting of a citric acid, ascorbic acid, maleic acid, lactic acid, and mixtures thereof.

54. The composition of claim 51 wherein the carboxylic acid salt comprises sodium lactate.

55. The composition of claim 51 wherein the carboxylic acid comprises an amino acid.

56. The composition of claim 55 wherein the amino acid is selected from the group consisting of glycine and β-alanine.

57. The composition of claim 51 wherein the amide is selected from the group consisting of urea, urea derivatives, and mixtures thereof.

58. The composition of claim 41 wherein the densifying agent comprises a blend of sorbitol and propylene glycol.

59. The composition of claim 41 wherein the densifying agent comprises a hygroscopic material.

60. The composition of claim 59 wherein the hygroscopic material is selected from the group consisting of halide salts of ammonium, aluminum, calcium, and iron; ammonium acetate; potassium acetate; and lithium citrate.

61. The composition of claim 41 further comprising superabsorbent material.

62. An absorbent article comprising a wood pulp composition comprising wood fibers having a fiber coarseness less than about 22 mg/100 In, wood fibers having a fiber coarseness greater than about 22 mg/100 m, and a densifying agent.

63. The absorbent article of claim 62 wherein the article is a diaper.

64. The absorbent article of claim 62 wherein the article is a feminine care product.

65. The absorbent article of claim 62 wherein the article is an adult incontinence product.

66. The absorbent article of claim 62 wherein the wood pulp composition further comprises superabsorbent material.

67. An absorbent article comprising a compressible wood pulp composition formed by applying a densifying agent to wood fibers having a fiber coarseness less than about 22 mg/100 m and wood fibers having a fiber coarseness greater than about 22 mg/100 m.

68. The absorbent article of claim 67 wherein the wood pulp composition further comprises superabsorbent material.

69. An absorbent article comprising a densified pulp product formed by compacting a fibrous web comprising a densifying agent and wood fibers having a fiber coarseness less than about 22 mg/100 m and wood fibers having a fiber coarseness greater than about 22 mg/100 m.

70. The absorbent article of claim 69 wherein the wood pulp composition further comprises superabsorbent material.

* * * * *